(12) United States Patent
Nagano et al.

(10) Patent No.: US 7,833,258 B2
(45) Date of Patent: Nov. 16, 2010

(54) THERMAL THERAPY DEVICE AND METHOD OF USE

(75) Inventors: Isamu Nagano, Kanazawa (JP); Kouichi Igarashi, Komatsu (JP)

(73) Assignees: Kanazawa University Technology Licensing Organization Ltd., Kanazawa-shi (JP); Komatu Power Tron Co., Ltd, Komatsu-shi (JP)

( * ) Notice: Subject to any disclaimer, the term of this patent is extended or adjusted under 35 U.S.C. 154(b) by 1063 days.

(21) Appl. No.: 11/578,954

(22) PCT Filed: Apr. 22, 2005

(86) PCT No.: PCT/JP2005/007718
§ 371 (c)(1),
(2), (4) Date: Oct. 19, 2006

(87) PCT Pub. No.: WO2005/102452
PCT Pub. Date: Nov. 3, 2005

(65) Prior Publication Data
US 2007/0179576 A1      Aug. 2, 2007

(30) Foreign Application Priority Data
Apr. 23, 2004    (JP)    .............................. 2004-128404

(51) Int. Cl.
*A61F 7/00*    (2006.01)

(52) U.S. Cl. .......................... 607/96; 607/101; 128/898
(58) Field of Classification Search .................. 607/88, 607/89, 96–116; 606/10–12, 32, 33; 128/898
See application file for complete search history.

(56) References Cited

U.S. PATENT DOCUMENTS 6,097,987 A * 8/2000 Milani .......................... 607/142
6,393,314 B1 * 5/2002 Watkins et al. ............... 600/411

FOREIGN PATENT DOCUMENTS

| | | |
|---|---|---|
| JP | A 7-022167 | 1/1995 |
| JP | A 2000-012340 | 1/2000 |
| JP | A 2002-360712 | 12/2002 |

* cited by examiner

*Primary Examiner*—Ahmed M Farah
(74) *Attorney, Agent, or Firm*—Oliff & Berridge, PLC

(57) ABSTRACT

The thermal therapy device comprises an inverter circuit connected to the primary side of a transformer, a series resonance circuit connected to the secondary side of the transformer and including a magnetic field generation coil and a resonance controller, and a controller for determining the resonance frequency based on the secondary current. The controller has a measurement mode and an operation mode which are alternately repeated. During the measurement mode the resonance frequency of the series resonance circuit is measured, while during the operation mode a drive signal of said measured resonance frequency is supplied from the controller to the inverter circuit.

11 Claims, 4 Drawing Sheets (a)

(b)

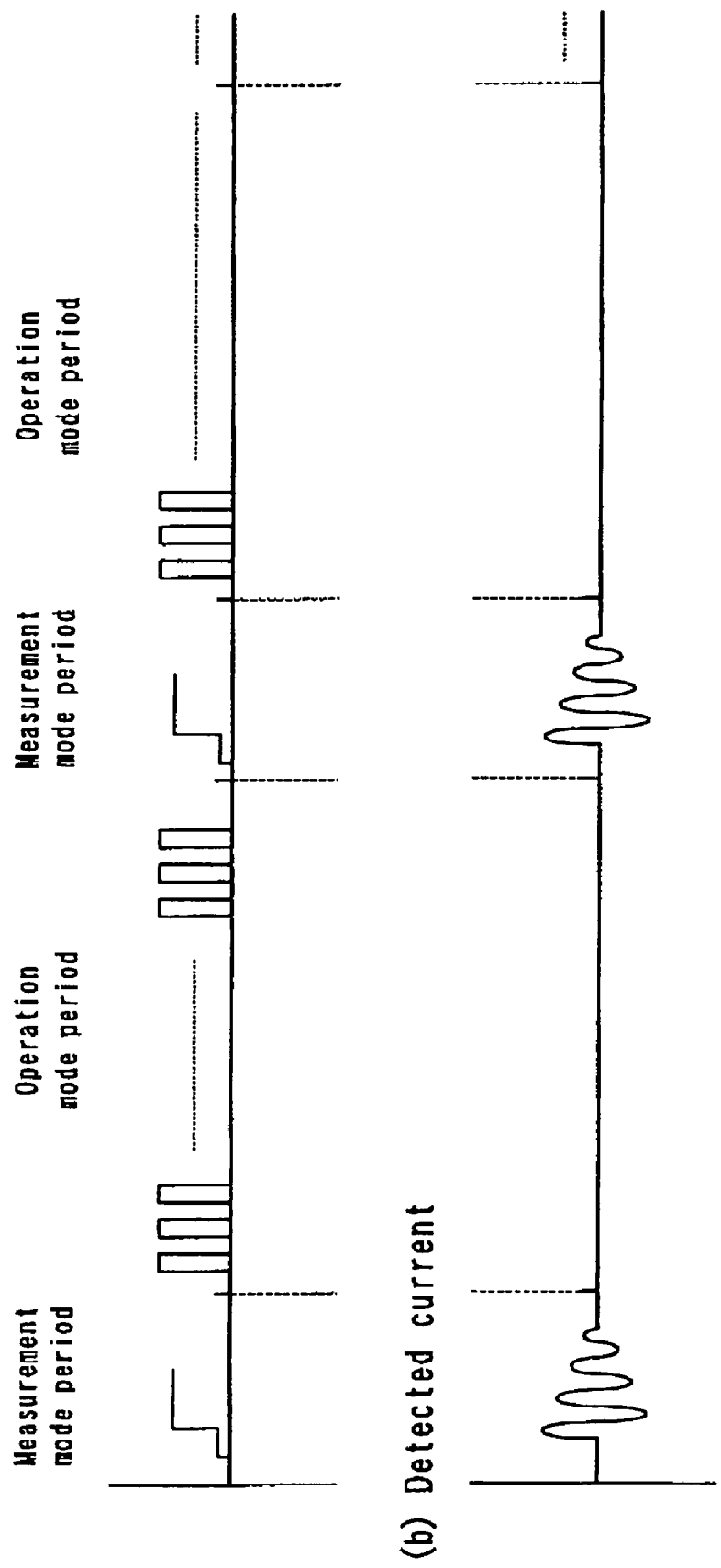

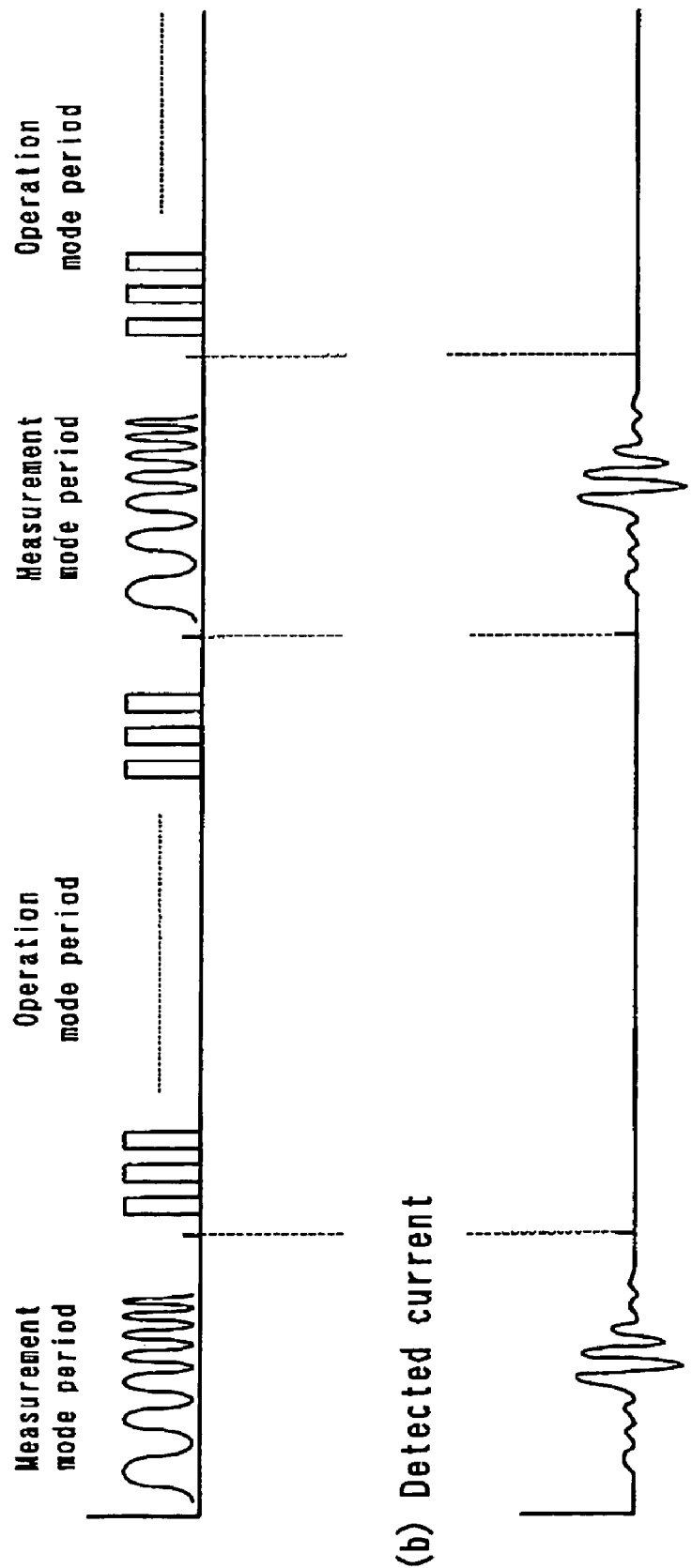

THERMAL THERAPY DEVICE AND METHOD OF USE

FIELD OF THE INVENTION

The present invention relates to a thermal therapy device that selectively heats the patient's affected portion, particularly to a thermal therapy device that is useful for cancer therapy.

BACKGROUND OF THE INVENTION

The thermal therapy (hyperthermia) method is attracting attention as a method for cancer therapy. As for this thermal therapy method, attention is focused upon the fact that a cancer cell or a cancerous tissue is more vulnerable to heat than a healthy cell. By heating the cancer-affected portion for example to 43 degree C. for a certain length of time, the cancer lesion can selectedly be necrotized. In this thermal therapy method, an aqueous sol of magnetic fluid comprising a complex of dextran or its derivative and magnetic iron oxide, dextran magnetite for example, is injected into the affected portion, to which a strong magnetic field is applied from outside to selectively heat the cancer lesion.

In such a method for therapy, in order to inductively heat the magnetic material having been injected into the affected portion, it is necessary to irradiate a strong magnetic flux from outside to the affected portion by using a magnetic field generation device. A magnetic field generation device preferable for such an inductive heating comprises a transformer, an inverter circuit connected to the primary side of the transformer and a series resonance circuit including a magnetic field generation coil and a resonance condenser connected to the secondary side of the transformer. The magnetic field generating device transmits through electromagnetic induction an alternate output of the inverter circuit connected to the primary side of the transformer to the series resonance circuit connected to the secondary side of the transformer. An alternate magnetic field is generated by applying a current of high frequency to the magnetic field generation coil. On this occasion, if the frequency of the alternate output transmitted to the series resonance circuit on the secondary side conforms with the resonance frequency of the series resonance circuit, the amount of current passing in the series resonance circuit is large enough to generate an alternate magnetic field of needed intensity at the magnetic field generation coil, making it possible to irradiate from the magnetic field generation coil a strong magnetic flux to the affected portion.

On the other hand, if the frequency of the alternate output transmitted to the series resonance circuit on the secondary side does not conform with the resonance frequency of the series resonance circuit, only a small amount of current passes in the series resonance circuit, failing to generate an alternate magnetic field of needed intensity at the magnetic field generation coil. Here, that the frequency of the alternate output transmitted to the series resonance circuit on the secondary side does not conform with the resonance frequency of the series resonance circuit means that the switching frequency of the inverter circuit does not conform with the resonance frequency of the series resonance circuit. In this case, the impedance on the primary side of the transformer becomes large, drastically reducing the electrical power transmitted from the primary side to the secondary side of the transformer as well as the amount of the current passing in the series resonance circuit, so that the intensity of the alternate magnetic field generated from the magnetic field generation coil is drastically decreased.

Inductance of the magnetic field generation coil may vary significantly according to factors like the size and the position of the affected portion. Accordingly, the true resonance frequency cannot be obtained by calculating the resonance frequency only based upon the design values of the magnetic field generation coil and the resonance condenser, which leads to a problem that a magnetic field of the needed intensity cannot be provided to the affected portion in cancer therapy. More importantly, according to various experiments and analyses concerning the series resonance circuit having been carried out by the inventor of the present invention, the inductance of the magnetic field generation coil and the capacity of the resonance condenser may vary from the design values according to environmental conditions such as temperature. A magnetic field of the needed intensity may not be generated during the whole therapy at the magnetic field generation coil if the switching frequency of the drive signal supplied to the inverter circuit is fixed based upon these design values. By thermal therapy, therefore, it is crucially important to make the switching frequency of the drive signal supplied to the inverter circuit follow accurately the resonance frequency of the series resonance circuit when the resonance frequency varies according to the size and the position of the affected portion and changes in the environmental conditions.

For the purpose of solving this problem, in the Japanese Patent Laid-open Publication No. 2002-360712 is disclosed a thermal therapy device in which the switching frequency of the drive signal supplied to the inverter circuit is conformed to the resonance frequency of the series resonance circuit. This thermal therapy device comprises a transformer, an inverter circuit connected to the primary side of the transformer, a series resonance circuit connected to the secondary side of the transformer which includes a magnetic field generation coil and a resonance condenser, and a PLL (phase locked loop) controlling unit for supplying a drive signal to the inverter circuit. The PLL controlling unit detects a current passing between the inverter circuit and the transformer (a current on the primary side) and generates a drive signal by PLL controlling in which the phase of the current on the primary side is compared with the phase of the drive signal so that the switching frequency of the drive signal to be provided to the inverter circuit is conformed with the resonance frequency of the series resonance circuit. With such a constitution, when the resonance frequency of the series resonance circuit varies according to changes in environmental conditions or the like, and the current on the primary side decreases, the PLL controlling unit generates the above mentioned drive signal in such a way that the current on the primary side has the same intensity as in the case that the frequency of the current on the secondary side conforms with the resonance frequency, in other words, in such a way that the switching frequency of the drive signal supplied to the inverter circuit conforms with the resonance frequency of the series resonance circuit. A current having the same frequency as the resonance frequency passes in the series resonance circuit. Therefore, if the resonance frequency of the series resonance circuit varies according to changes in environmental conditions or the like, the switching frequency of the drive signal provided to the inverter circuit can follow the resonance frequency.

DISCLOSURE OF THE PRESENT INVENTION

Problems to be Solved

However, in order to apply a strong magnetic flux to the affected portion, the magnetic field generation coil should be attached in an appropriate way, for example by folding the magnetic field generation coil about the patient's affected portion. In this case, it is necessary to change flexibly the length or the diameter of the magnetic field generation coil according to the position of the patient's affected portion and the patient's body shape, which will bring about a significant change in the resonance frequency.

With the use of the above described thermal therapy device in such a case, since the PLL unit of the thermal therapy device comprises an analog circuit, it is impossible to generate with certainty a drive signal of such a switching frequency as to follow the varying resonance frequency. More specifically, the magnetic field generating device as described above cannot be applied if the load variation ranges widely and the resonance frequency varies significantly.

The present invention is intended to provide a thermal therapy device that can follow with certainty changes in the resonance frequency even if the load variation ranges widely and the resonance frequency of the series resonance circuit on the secondary side varies significantly, and generate a magnetic field of needed intensity for heating the affected portion.

Means for Solving the Problem

The present invention relates to a thermal therapy device comprising a transformer, an inverter circuit connected to the primary side of said transformer, a series resonance circuit connected to the secondary side of said transformer and including a magnetic field generation coil and a resonance condenser, a controller for providing a drive signal to said inverter circuit in such a way that the frequency of the current passing in said series resonance circuit conforms with the resonance frequency thereof and a current detecting device for detecting a current passing in said series resonance circuit, wherein said magnetic field generation coil generates a magnetic field of high frequency towards the patient's affected portion. The controller comprises a mode setting means for switching alternately between an operation mode during which a magnetic field of high frequency is generated towards the patient's affected portion and a measurement mode during which the resonance frequency of said series resonance circuit is measured to set the mode, a resonance frequency determining means for receiving an input of a signal of a current having been detected by said current detecting means during the measurement mode set by said mode setting means to determine said resonance frequency based on said signal and a drive signal supplying means for supplying to said inverter circuit a drive signal of a switching frequency based on said resonance frequency having been determined by said resonance frequency determining means during the operation mode set by said mode setting means.

According to the present invention, since the measurement mode during which the resonance frequency of the series resonance circuit is measured and the operation mode during which the inverter circuit is driven with the switching frequency based on the measured resonance frequency are alternately repeated, even if the resonance frequency of the series resonance circuit varies this varying resonance frequency can be followed by the switching frequency of the inverter circuit. As a result, a magnetic field of needed intensity for thermal therapy can be generated during the whole therapy.

A preferred embodiment of the present invention can be characterized in that the controller supplies to the inverter circuit a drive signal of a step voltage or a white noise during the period of the measurement mode. The embodiment can as well be characterized in that a sweep signal of sequentially changing frequency is supplied to the inverter circuit as a drive signal during the period of the measurement mode.

Further, the embodiment can be characterized in that during the period of measurement mode the controller receives an input of a signal of the current having been detected by the current detecting means and subjects said signal to a frequency analysis using fast Fourier transformation to obtain a frequency spectrum and determine said resonance frequency.

BRIEF DESCRIPTION OF THE DRAWINGS

FIG. 3 is a timing chart showing an example of the operation of the thermal therapy device of the present invention.

FIG. 4 is a timing chart showing another example of the operation of the thermal therapy device of the present invention.

DESCRIPTION OF THE PREFERRED EMBODIMENTS

Figure 1:
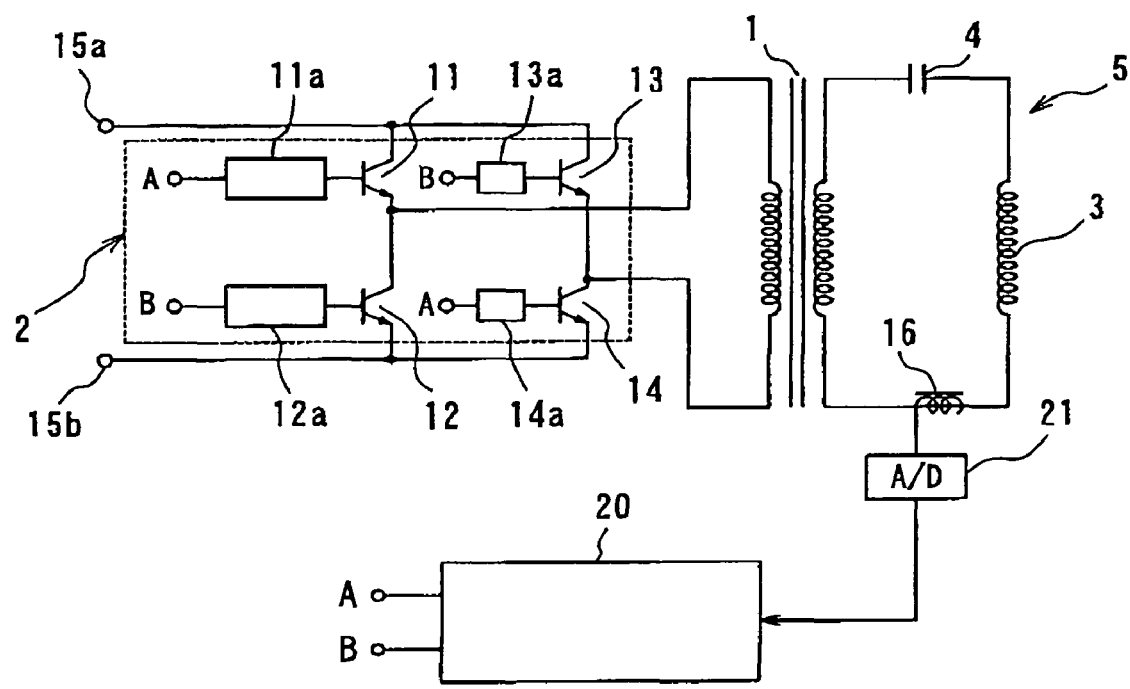
FIG. 1 is a constitution diagram showing an example of the thermal therapy device of the present invention.

FIG. 1 is a constitution diagram showing an example of the thermal therapy device of the present invention. The thermal therapy device comprises a transformer 1, an inverter circuit 2 connected to the primary side of the transformer 1, a series resonance circuit 5 connected to the secondary side of the transformer 1, a current probe 16 for detecting a current passing in the series resonance circuit 5, an A/D converter 21 and a controller 20 for supplying a drive signal to the inverter circuit 2. The series resonance circuit 5 includes a magnetic field generation coil 3 and a resonance condenser 4. The inverter circuit 2 is an inverter circuit in the shape of an H-bridge and comprises four transistors 11 to 14 that operate as switching elements and four driver circuits 11a, 12a, 13a and 14a each driving each of the transistors 11 to 14 respectively. The inverter circuit 2 is provided with input terminals 15a and 15b which are applied with direct-current voltage.

The controller 20 comprises a means for receiving an input of the value of the current having been detected with the current probe 16 provided to the series resonance circuit 5, a means for subjecting the current value to a frequency analysis process using fast Fourier transformation to obtain a frequency spectrum, a means for determining the resonance frequency of the series resonance circuit 5 based on the frequency spectrum, a means for generating a drive signal of the resonance frequency and supplying it to the inverter circuit 2 and a means for switching between the operation mode and the measurement mode to set the mode. The controller 20 generates a drive signal of such a switching frequency as to conform with the resonance frequency so that the frequency of the current passing in the series resonance circuit 5 conforms with the resonance frequency of the series resonance circuit. By supplying the drive signal to the inverter circuit 2, a current of the same frequency as the resonance frequency to the series resonance circuit 5 is applied from the inverter circuit 2 via the transformer 1. In this embodiment, for example, a high-frequency alternate current of 400 kHz and 500 V is applied to the magnetic field generation coil 3 on the secondary side of the transformer 1. With this, a strong magnetic field is generated from the magnetic field generation coil 3 towards the patient's affected portion. With the above explained magnetic fluid injected in advance into the patient's affected portion, the affected portion can selectedly be heated by an interaction between the magnetic field generated from the magnetic field generation coil 3 and the magnetic particle having been injected into the affected portion.

The operation of the thermal therapy device as shown in FIG. 1 will be explained next. To the input terminals 15a and 15b provided to the inverter circuit 2 is applied a direct current of 500 V. The inverter circuit 2 transmits through electromagnetic induction the alternate output according to the drive signal from the controller via the transformer 1 to the series resonance circuit 5 on the secondary side. A current of high frequency is applied to the magnetic field generation coil 3 to generate an alternate magnetic field.

The current probe 16 detects a current in the series resonance circuit 5. The A/D converter 21 converts the current having been detected with the current probe 16 into a digital signal and output it to the controller 20. The digital signal of the current having been converted by the A/D converter is input to the controller 20 to be subjected to a frequency analysis using fast Fourier transformation, from which a frequency spectrum is obtained and the resonance frequency of the series resonance circuit 5 is determined. The controller 20 further generates drive signals A and B of the obtained resonance frequency, which are then provided to the driver circuits 11a, 12a, 13a and 14a of the inverter circuit 2. In other words, the controller 20 controls the drive frequency of the drive signals A and B so that the frequency conforms with the resonance frequency of the series resonance circuit 5, the drive signals A and B being then provided to the inverter circuit 2. The inverter circuit 2 is thus driven with a switching frequency being equal to the resonance frequency of the series resonance circuit 5.

The therapy operation mode may be the operation mode during which the device generates a magnetic field of high frequency from the magnetic field generation coil 3 towards the affected portion or the measurement mode during which the resonance frequency of the series resonance circuit 5 is measured. The controller 20 comprises a means for switching and selecting the mode to alternately repeat the operation mode and the measurement mode. During the measurement mode, the controller 20 subjects the current passing in the series resonance circuit 5 which has been detected with the current probe 16 during that period to an frequency analysis using fast Fourier transformation and determines the resonance frequency of the series resonance circuit 5 based upon the obtained frequency spectrum.

The series resonance circuit 5 has such a characteristic that the impedance thereof drastically decreases at the resonance frequency, while the impedance is quite large in the other frequency range than the resonance frequency. Accordingly, if a voltage to be transmitted to the secondary side of the transformer 1 includes a smaller fundamental frequency than the resonance frequency and harmonic components of higher frequency than the resonance frequency, the current passing in the series resonance circuit 5 will only consist of a component having the same frequency as the resonance frequency among the components transmitted to the secondary side. Thus, the current passing in the series resonance circuit 5 on the secondary side becomes a sine wave of the same frequency as the resonance frequency. The present invention can be characterized in that it makes use of this behavior. More particularly, the controller 20 applies a step voltage to the inverter circuit 2 during the measurement mode. With this, a current of the same frequency as the resonance frequency among harmonic components appearing at the rising edge of the step voltage is applied on the secondary side, generating a resonance current. The current probe 16 then detects this resonance current, and the controller 20 subjects the current to a frequency analysis using fast Fourier transformation to obtain the frequency spectrum, based on which the resonance frequency of the series resonance circuit 5 is determined.

Thus, because the controller 20 can easily apply a step voltage to the inverter circuit 2, the resonance frequency of the series resonance circuit 5 can be determined with a simple mechanism.

In addition, a white noise may also be applied with the controller 20 instead of a step voltage during the measurement mode. The resonance frequency of the series resonance circuit can also be determined by the controller 20 in this case.

During the operation mode, the controller 20 applies a drive signal of the same frequency as the resonance frequency of the series resonance circuit 5 having been obtained during the measurement mode to the inverter circuit 2. With this constitution, the controller 20 can make the frequency of the drive signal applied to the inverter circuit 2 follow the resonance frequency if the resonance frequency of the series resonance circuit 5 varies during thermal therapy.

Figure 2:
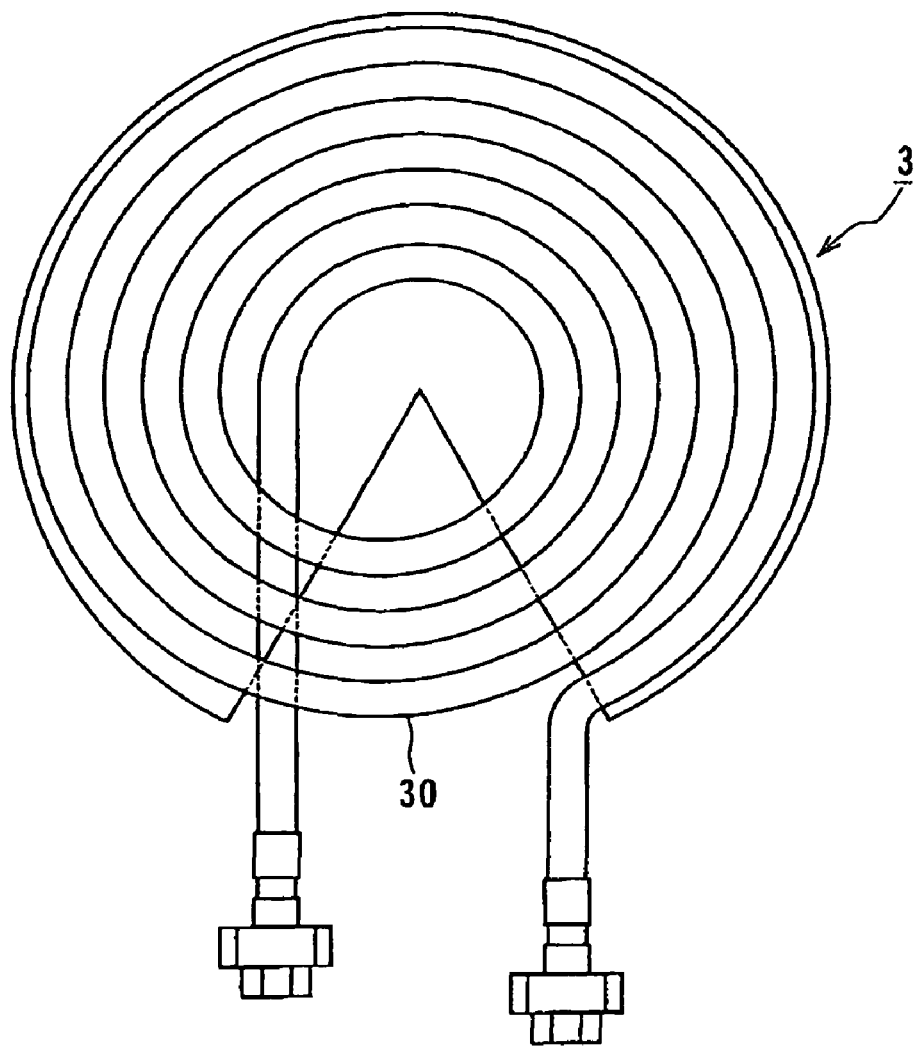
FIG. 2 is a schematic diagram showing an example of the magnetic field generation coil.
Figure 2:
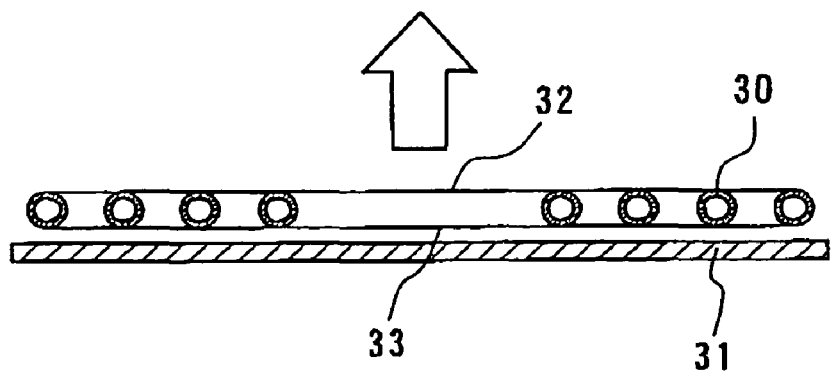

FIG. 2(a) and FIG. 2(b) are schematic diagrams of a magnetic field generation coil 3 for generating a magnetic field towards the patient's affected portion. The magnetic field generation coil 3 is a bread-shaped coil device having a current path in the shape of a spiral in a substantially same plane (the coil plane). In addition, the magnetic field generation coil 3 comprises a flexible material so that a strain is not to be imposed upon the patient. More particularly, it comprises a bundle of entwisted wires like a litz wire in which a plurality of isolated thin conductive wires are bundled and entwisted. Such a bundle of entwisted wires having flexibility, the magnetic field generation coil 3 can change the length or the diameter according to the position of the affected portion or the patient's body shape, so that it can be folded about the body surface around the patient's affected portion. On the downside of the bread-shaped coil 30 is placed a core plate 31 of a high-permeability material. As a high-permeability material is used for example ferrite. The core plate 31 has a greater square measure at the surface thereof facing the bread-shaped coil 30 than the coil surface 33 of the bread-shaped coil 30. Since the magnetic flux generated downward from the coil surface 33 of the bread-shaped coil 30 is reflected on the core plate 31 with this constitution, the magnetic flux generated from the bread-shaped coil 30 is integrated into a magnetic flux directing upward from the coil surface 32, the magnetic field being thus concentrated on the upper side of the coil surface 32. As a result, the thermal therapy device can effectively apply the magnetic field to the patient positioned opposite to the core plate 31.

The operation mode of the thermal therapy device will be explained next. FIG. 3(a) and FIG. 3(b) are timing diagrams showing the drive signal applied from the controller 20 to the inverter circuit 2 and the current on the secondary side (the detected current) having been detected with the current probe 16 to be input to the controller 20. The therapy operation mode of the thermal therapy device will be the operation mode during which a magnetic field of high frequency is generated toward the affected portion or the measurement mode during which the resonance frequency of the series resonance circuit 5 is measured. The controller 20 alternately switches between the operation mode and the measurement mode. With reference to FIG. 3(a) and FIG. 3(b), for example, the time period of the measurement mode can be set to 2 sec., and the time period of the operation mode to 28 sec. During the measurement mode the controller 20 applies a step voltage to the inverter circuit 2. A white noise can also be applied instead. As is shown in FIG. 2(b), as controller 20 applying a step voltage to the inverter circuit 2, the current probe 16 can detect a resonance current having the same frequency as the resonance frequency of the series resonance circuit 5. The controller 20 determines during the measurement mode the frequency of the resonance current having been detected with the current probe 16.

The thermal therapy device switches to the operation mode at the end of the measurement mode. The controller 20 applies to the inverter circuit 2 a drive voltage having the same frequency as that of the resonance current having been detected during the measurement mode, i.e., the same frequency as the resonance frequency of the series resonance circuit. Thus by alternately switching between the measurement mode and the operation mode, even if the resonance frequency of the series resonance circuit varies, the switching frequency of the inverter circuit 2 can follow the change in the resonance frequency.

A modified example of the thermal therapy device of the present invention will be explained next. Although this thermal therapy device is given a similar constitution as the thermal therapy device as shown in FIG. 1, it is not a step voltage or a white noise that is applied by the controller 20 as a drive voltage during the measurement mode, but a sweep voltage (an FM wave) of frequency changing with time. The value of the resonance frequency of the series resonance circuit 5 including the magnetic field generation coil 3 and the resonance condenser 4, as well as the variation range of the resonance frequency that is varying according to environmental conditions, can be known in advance as a design value. In this modified example, the controller 20 stores in advance a sweep frequency signal having the center frequency of the resonance frequency as an estimated design value, and a drive signal of a sweep voltage with the stored sweep frequency is applied to the inverter circuit 2 during the measurement mode.

When the drive signal of the sweep voltage with changing frequency is applied from the controller 20 to the inverter circuit 2, there appears very little current passing in the series resonance circuit 5 on the secondary side if the range of frequency of the sweep voltage of the applied drive signal is away from the resonance frequency. On the other hand, if the frequency of the sweep voltage of the applied drive signal conforms with the resonance frequency, a current of the resonance frequency passes instantly in the series resonance circuit 5. This resonance current is detected with the current probe 16 to be subjected by the controller 20 to a frequency analysis using fast Fourier transformation to obtain a frequency spectrum and determine the resonance frequency of the series resonance circuit 5.

The controller 20 applies during the operation mode to the inverter circuit 2 a drive signal with the same frequency as the resonance frequency of the series resonance circuit 5 that has been obtained during the measurement mode. With this constitution, the controller 20 can make the frequency of the drive signal to be applied to the inverter circuit 2 follow the resonance frequency.

FIG. 4(*a*) and FIG. 4(*b*) are timing diagrams of the modified example of the thermal therapy device of the present invention which shows the drive signal supplied from the controller 20 to the inverter circuit 2 and the current on the secondary side (the detected current) having been detected with the current probe 16 to be input to the controller 20. The operation mode of the thermal therapy device may be the operation mode during which a magnetic field of high frequency is generated toward the affected portion or the measurement mode during which the resonance frequency of the series resonance circuit 5 is measured, which are alternately repeated. During the measurement mode the controller 20 applies a sweep voltage to the inverter circuit 2. As the controller 20 applies the sweep voltage to the inverter circuit 2, a current of the resonance frequency passes in that very moment in the series resonance circuit if the frequency of the sweep voltage conforms with the resonance frequency, the resonance current being detected with the current probe 16. The controller 20 determines during the measurement mode the frequency of the resonance current having been detected with the current probe 16. With the use of the controller 20 that supplies a sweep voltage of sequentially changing frequency to the inverter circuit 2 and detects the resonance frequency, the degree of detection accuracy of the resonance frequency can further be increased.

As described above, according to the embodiments of the thermal therapy device of the present invention, with the use of the controller 20 that supplies as a drive voltage a step voltage, a white noise or a sweep voltage to the inverter circuit 2, the resonance frequency is determined by inputting the digital value of the current on the secondary side. The resonance frequency is obtained with the CPU provided to the controller 20 in a series of processes of subjecting the digital value of the secondary current to a frequency analysis using fast Fourier transformation and obtaining a frequency spectrum. Thus, according to an example of the thermal therapy device of the present invention, the above-described series of processes are carried out by a computer (a personal computer, for example) as a controller 20. Accordingly, even if the load varies according to environmental conditions to change the resonance frequency of the series resonance circuit 5, the resonance frequency can be determined by sweeping the frequency over a wide range, thus enabling handling of a wide range of frequency.

The resonance frequency of the magnetic field generation coil 3 may especially be changeable because of its flexibility and its ability to change shape to fit the position of the patient's affected portion and the patient's body shape. In such a case, as described previously, the thermal therapy device of the prior art as described in the Japanese Patent Laid-open Publication No. 2002-360712 cannot handle the load change in a wide range. With the thermal therapy device of the present invention, the frequency can be swept over a wide range with the use of the CPU provided to the controller 20, and the change in the resonance frequency can adequately be followed even if the load change is wide-ranging.

The invention claimed is:

1. A thermal therapy device comprising a transformer, an inverter circuit connected to the primary side of said transformer, a series resonance circuit having a resonance frequency, connected to the secondary side of said transformer and including a magnetic field generation coil and a resonance condenser and a controller for supplying a drive signal to said inverter circuit in such a way that the frequency of a current passing in said series resonance circuit conforms with the resonance frequency thereof, the device generating a magnetic field of high frequency toward a patient's affected portion;

wherein said thermal therapy device comprises a current detecting means for detecting the current passing in said series resonance circuit; and said controller comprises a mode setting means for alternately switching between an operation mode during which a magnetic field of high frequency is generated toward the patient's affected portion and an measurement mode during which the resonance frequency of said series resonance circuit is measured to set the mode, a resonance frequency determining means for receiving an input of a signal of a current having been detected by said current detecting means and determining said resonance frequency based upon said signal during the measurement mode set by said mode setting means, and a drive signal supplying means for supplying a drive signal of a switching frequency to said inverter circuit using the resonance frequency having been determined by said resonance frequency determining means during the operation mode set by said mode setting means.

2. The thermal therapy device according to claim 1, wherein the drive signal supplied by said drive signal supplying means is a step signal or a white noise signal.

3. The thermal device according to claim 1, wherein the drive signal supplied by said drive signal supplying means is a sweep signal of sequentially changing frequency.

4. The thermal therapy device according to claim 1, wherein said resonance frequency determining means receives the current signal having been detected by the current detecting means and subjects said signal to a frequency analysis using fast Fourier transformation to obtain a frequency spectrum and determine said resonance frequency during the measurement mode set by the mode setting means.

5. The thermal therapy device according to claim 1, wherein said magnetic field generation coil is a bread-shaped coil having a current path that extends in the shape of a spiral in the coil plane.

6. The thermal therapy device according to claim 5, further comprising a core plate facing the coil surface opposite to the patient's affected portion, seen from said magnetic field generation coil.

7. The thermal therapy device according to claim 5, wherein said magnetic field generation coil has the flexibility and changes shape.

8. A thermal therapy method for generating a magnetic field of high frequency using a transformer, an inverter circuit connected to the primary side of said transformer, a series resonance circuit having a resonance frequency, connected to the secondary side of said transformer and including a magnetic field generation coil and a resonance condenser and a controller for supplying a drive signal to said inverter circuit in such a way that the frequency of a current passing in said series resonance circuit conforms with the resonance frequency thereof, comprising the steps of:

alternately switching between an operation mode during which a magnetic field of high frequency is generated toward a patient's affected portion and a measurement mode during which the resonance frequency of said series resonance circuit is measured to set the mode;

determining the resonance frequency by receiving an input of a signal of a current passing in said series resonance circuit during said measurement mode;

supplying a drive signal of a switching frequency based on the determined resonance frequency to said inverter circuit during the operation mode;

generating the magnetic field of high frequency, the magnetic field being generated by the magnetic field generating coil when the drive signal is supplied to the inverter circuit during the operation mode; and applying a magnetic field of the high frequency toward the patient's affecting portion during the operation mode.

9. The thermal therapy method according to claim 8, wherein said drive signal is a step signal or a white noise signal.

10. The thermal therapy method according to claim 8, wherein said drive signal is a sweep signal of sequentially changing frequency.

11. The thermal therapy method according to claim 8, wherein said step of determining the resonance frequency is a step of determining said resonance frequency by receiving an input of a signal of a current passing in said series resonance circuit and subjecting said signal to a frequency analysis using fast Fourier transformation to obtain a frequency spectrum.

* * * * *